(12) United States Patent
Ostrin

(10) Patent No.: US 11,375,890 B2
(45) Date of Patent: Jul. 5, 2022

(54) SYSTEMS AND METHODS FOR CONTINUOUS OBJECTIVE ASSESSMENT OF NEAR WORK

(71) Applicant: University of Houston System, Houston, TX (US)

(72) Inventor: Lisa Ostrin, Houston, TX (US)

(73) Assignee: University of Houston System, Houston, TX (US)

( * ) Notice: Subject to any disclaimer, the term of this patent is extended or adjusted under 35 U.S.C. 154(b) by 235 days.

(21) Appl. No.: 16/229,458

(22) Filed: Dec. 21, 2018

(65) Prior Publication Data

US 2019/0191989 A1 Jun. 27, 2019

Related U.S. Application Data

(60) Provisional application No. 62/608,755, filed on Dec. 21, 2017.

(51) Int. Cl.
*A61B 3/028* (2006.01)
*G01J 1/42* (2006.01)
(Continued)

(52) U.S. Cl.
CPC ............ *A61B 3/028* (2013.01); *A61B 3/0041* (2013.01); *A61B 3/152* (2013.01); *A61B 5/6898* (2013.01); *G01J 1/4204* (2013.01)

(58) Field of Classification Search
CPC ....... A61B 3/032; A61B 3/0285; A61B 3/028; A61B 3/0025; A61B 3/0091; A61B 3/024;
(Continued)

(56) References Cited

U.S. PATENT DOCUMENTS 6,450,643 B1 * 9/2002 Wilson .................. A61B 3/028
351/223
8,016,416 B1 * 9/2011 Straus .................. A61B 5/1171
351/200
(Continued)

FOREIGN PATENT DOCUMENTS

EP 3228237 † 11/2017

OTHER PUBLICATIONS http://www.clouclip.com/.
Leung, et al., "A novel instrument for logging network distance", Ophthalmic & Physiological Optics, pp. 137-144, 2011, The College of Optometrists.†

*Primary Examiner* — William R Alexander
*Assistant Examiner* — Sharrief I Broome
(74) *Attorney, Agent, or Firm* — Shackelford, Bowen, McKinley & Norton, LLP

(57) ABSTRACT

Systems and methods for continuous objective assessment are discussed herein. The systems and methods may comprise sensor(s), a processor, a clock, data storage, and a power source. The sensor(s) may continuously monitor viewing distances, light exposure, or the like, and the system may log corresponding time and/or duration information. Also provided herein are methods of treating, preventing, and/or diagnosing vision impairment risk. These systems and methods may provide warns, such as when detecting the viewing of materials too closely (e.g. ≤30 cm), near to near intermediate viewing (e.g. ≤70 cm) exceeding a predetermined time (e.g. ≥20 min.) without a break, and/or not getting enough outdoor light exposure (e.g. at least 75 minutes of exposure at >1000 lux) for the day.

18 Claims, 3 Drawing Sheets

(51) Int. Cl.
*A61B 3/00* (2006.01)
*A61B 5/00* (2006.01)
*A61B 3/15* (2006.01)

(58) Field of Classification Search
CPC ......... A61B 3/103; A61B 3/0033; A61B 3/04;
A61B 3/08; A61B 3/0041; A61B 3/022;
A61B 3/02; A61B 3/101; A61B 5/16;
A61B 3/0008; A61B 3/036; A61B
3/1015; A61B 3/113; A61B 3/14; G02C
7/02; G02C 2202/22; G02C 7/061; G02C
13/005; G02C 11/10; G02C 2202/10;
G02C 2202/12; G02C 2202/16; G02C
2202/18; G02C 2202/20; G02C 7/022;
G02C 7/049; G02C 7/06; G02C 7/066;
G02C 7/083; G02C 7/101; G02C 7/102;
G02C 13/003; G02C 7/04; G02C 7/104
See application file for complete search history.

(56) References Cited

U.S. PATENT DOCUMENTS

| | | | | |
|---|---|---|---|---|
| 8,328,420 | B2 * | 12/2012 | Abreu | A61B 5/01 374/208 |
| 2003/0223038 | A1 * | 12/2003 | Alster | A61B 3/032 351/211 |
| 2005/0225720 | A1 * | 10/2005 | Ridings | A61B 3/032 351/200 |
| 2009/0105605 | A1 * | 4/2009 | Abreu | A61B 5/0046 600/549 |
| 2019/0142268 | A1 * | 5/2019 | Zakharov | A61B 5/06 351/239 |

\* cited by examiner
† cited by third party

SYSTEMS AND METHODS FOR CONTINUOUS OBJECTIVE ASSESSMENT OF NEAR WORK

RELATED APPLICATIONS

This application claims the benefit of U.S. Provisional Patent Application No. 62/608,755 filed on Dec. 21, 2017, which is incorporated herein by reference.

FIELD OF THE INVENTION

The present disclosure relates to systems and methods continuous objective assessment, including near work.

BACKGROUND OF INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Light exposure and near work are known risk factors for myopia. Current technology allows for objective measurements of light exposure; however, quantification of near work is typically assessed via questionnaires, which are subject to poor recall and biases. Additionally, it is not possible to evaluate viewing behavior from questionnaires. Thus, there remains a need in the art for systems and methods that provides continuous, objective measurement of near work to quantify risk factors related to myopia, and/or to provide feedback to the wearer when the working distance is too close or a distance viewing break should be initiated.

SUMMARY OF INVENTION

Various embodiments disclosed herein include a system for continuous objective assessment. The system may comprise sensor(s), a processor, a clock, data storage, and a power source. The sensor(s) may continuously monitor viewing distances, light exposure, and/or the like. The system may log corresponding time and/or duration information. For example, they system may provide an infrared time-of-flight (TOF) distance sensor operatively connected to a real time clock controlled by a microprocessor coupled to a digital card data logger. In one embodiment, the TOF distance sensor has nanosecond technology. In one embodiment, the microprocessor is an Arduino microprocessor. In one embodiment, the digital card data logger is a micro secure digital card data logger. In one embodiment, the device further comprises a lithium polymer battery. In one embodiment, the system is removably mounted on a spectacle frame. In one embodiment, the system is removably mounted on a temple of a spectacle frame. In one embodiment, the system further comprises an alarm, and wherein the alarm is set off by the system when the distance measured by the TOF distance sensor is less than a predetermined reference distance. In one embodiment, the system further comprises an alarm, and wherein the alarm is set off when the distance measured by the TOF distance sensor remains below a predetermined reference distance over a predetermined duration. In one embodiment, the microprocessor and/or the digital card data logger are wirelessly connected to the TOF distance sensor and the real time clock.

Various embodiments disclosed herein also include a method of diagnosing, treating, preventing, minimizing the risk of, and/or treating vision impairment in a subject. The method may comprise positioning a distance sensor to continuously measure viewing distances; capturing time data associated with the viewing distances measured; storing the time data and the viewing distances measured. Further, the viewing distance measurements and time data may be analyzed to diagnose vision impairment risks. In one embodiment, the vision impairment is an eye disease. In one embodiment, the vision impairment is myopia. In one embodiment, the systems or method may include an alarm. In some embodiments, the alarm is set off by the device when the distance measured by the distance sensor is less than a pre-determined reference distance. In one embodiment, the alarm is set off when the distance measured by the distance sensor remains below a predetermined reference distance over a predetermined duration. In one embodiment, the device allows measurement of refractive error development based on viewing behavior. In one embodiment, the microprocessor and/or the digital card data logger are wirelessly connected to the TOF distance sensor and the real time clock.

Other features and advantages of the invention will become apparent from the following detailed description, taken in conjunction with the accompanying drawings, which illustrate, by way of example, various embodiments of the invention.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
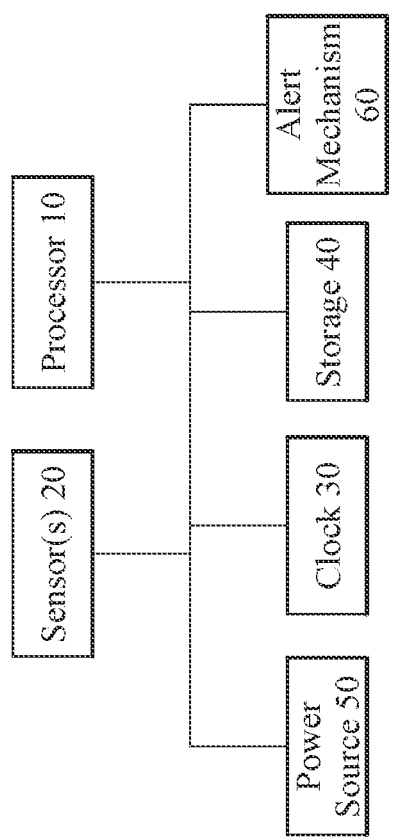
FIG. 1 shows a block diagram of a system for continuous objective assessment.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

As described herein, in accordance with the various embodiments herein, novel systems or method for continuous objective assessment of near work are discussed herein. a distance sensor, a clock, a processor, storage, and/or power source. As a nonlimiting example, an infrared time-of-flight (TOF) distance sensor and real-time clock (RTC) controlled by an Arduino microprocessor coupled to a micro secure digital card data logger may be utilized. The storage may include coding suitable for performing the various desired operations discussed further herein. For example, open-source programming libraries for the TOF, RTC, and data logger components may be used to supply code for the device. As a nonlimiting example, power may be supplied by a rechargeable lithium polymer battery to provide greater than 16 hours of continuous distance logging at 1 Hz.

In one embodiment, the systems and methods provides accurate, continuous and objective measurements of near working distances. The systems and methods exhibit a linear calibration function and a small beam diameter, which increases the accuracy of detecting the target that is being viewed. In some embodiments, measured working distances can be binned in 10 cm intervals from 10 cm to <100 cm, with values 100 cm or greater being considered "distance viewing," and a corresponding near work classification system was developed. In one embodiment, wireless technology is incorporated into the device. Further, near work behaviors between emmetropic and myopic adults and children are characterized to understand potential influences of viewing behavior on refractive error development. In some embodiment, the device may alert the wearer when the viewing distance is too close or a viewing break should be implemented through haptic feedback or the like, e.g. vibration alert. As a nonlimiting example, the alert may be audio, visual, haptic, or combinations thereof.

An embodiment of a system for continuous objective assessment is shown in FIG. 1 and discussed further herein. The system may provide objective assessment of near work, light exposure, and/or the like. The system provides a processor 10, which may be any suitable processor, controller, or the like, that controls various operations of the system discussed further herein. Processor 10 may be coupled to the various components of the system, such as, but not limited to, sensor(s) 20, clock 30, storage 40, power source(s) 50, and alert mechanism 60. It shall be understood that coupling refers to operatively connected components, which includes direct or indirect physical connections, wireless connections, or both. As the system may be mounted to spectacle frames, thereby making weight a concern, some components of the system coupled together wirelessly via transmitter(s), receiver(s), and/or transceiver(s) so that some components may be positioned remotely away from the frames. As a nonlimiting example, sensor(s) 20 may be mounted to the spectacle frame and may communicate wirelessly via a transceiver, transmitter, or the like with other components provided in a separate housing, such as a belt clip enclosure. One or more sensor(s) 20 provide desired measurement of parameters of interests.

As nonlimiting examples of sensor(s) 20, a distance sensor (e.g. infrared IR TOF sensor) may be desirable to measure distance of objects for near work measurements and/or a light intensity sensor may be desirable for measuring broadband (e.g. white) light exposure. TOF sensors determine distance by using the duration between transmission of a signal and return of a reflected signal. The light sensor may detect illuminance of broadband (white) light. For example, the light sensor may detect from 0.1 to 200,000 lux. Further, when sensor(s) 20 detect a parameter of interests, such as distance below a predetermined value, distance in a predetermined range, and/or light exposure exceeding a predetermined amount, an event may be logged. Nonlimiting examples of events of interest may comprise viewing materials too closely (e.g. ≤30 cm), near intermediate viewing or less (e.g. ≤70 cm) exceeding a predetermined time (e.g. ≥20 min.) without a break, and/or not getting enough outdoor light exposure (e.g. at least 75 minutes of exposure at >1000 lux) for the day. Clock 30 is utilized to log time data and/or duration of event(s) of interests. Based on the time data logged, the system can easily determine duration of the event(s) of interest. As nonlimiting examples, the clock 30 may be utilized to log duration of viewing distances in a particular range or class, duration of viewing distances closer than a particular distance, and/or exposure to light exceeding a specific level. Storage 40 may provide programming for the various operations of the system, storage for collected data, or the like. Power source 50 provides electric power for the system. Alert mechanism 60 provides desired alert(s) to the wearer when desired. The alert(s) may be audio, visual, haptic, or combinations thereof. Further, the alerts may differ depending on the event-of-interest, such as varying in audio tone, visually, haptic pattern, or the like. Nonlimiting examples of risk behaviors that may trigger alerts comprise (1) reading materials too closely (e.g. ≤30 cm); (2) spending too much time near to near intermediate viewing (e.g. ≤70 cm) without taking a break to shift to distance viewing (≥100 cm); and/or (3) not getting enough outdoor exposure in a day (e.g. ≥75 minutes), and more particularly by a certain time (e.g. 4 pm).

In some embodiments, the sensor device(s) is/are removably mounted on a frame or spectacle frame, which shall be understood to mean frames with or without corrective lenses. In some embodiments, the system is removably mounted on a temple of a spectacle frame. For example, the sensor component(s) is/are mounted on frames near the temple, and may be directed nasally or to focus centrally at a desired angle (e.g. approximately 4°) so that the beam is aligned at a desired midpoint (e.g. 0.40 m). In some embodiments, the system further comprises an alert or alarm, and wherein the alert or alarm is set off by when the distance measured by the TOF distance sensor is less than a predetermined reference distance. As a nonlimiting example, the reference distance may be 30 cm or less, 70 cm or less, or any other distance. Further, the logging of time data or duration of events of interest allows for monitoring duration of events. For example, alerts may also be triggered by near to near intermediate viewing (e.g. ≤70 cm) exceeding a predetermined time (e.g. ≥20 min.) without a break or not getting enough outdoor light exposure (e.g. at least 75 minutes of exposure at >1000 lux) for the day. Other components of the system may be secured in any suitable manner possible, such as with a housing with a belt clip, pocket sized housing, or the like, which may allow minimal weight to be added to the frames. In some embodiments, the system may categorize gathered data on viewing distances into two or more classes (e.g. near, intermediate, and far). Other embodiments may provide several classes (e.g. see Table 1). Data may be gather continuously, and may optionally be separated into set time intervals. Gathered data may be downloaded to suitable remote device (e.g. PC, laptop, remote storage device, etc.), such as nightly, either manually, automatically, and/or wirelessly. In some embodiments, objective diopter hours may be calculated (see Eq. 1). Further, some embodiments may provide an alarm based on diopter hours equal to or exceeding a predetermined value.

In some embodiments, the system further comprises an alarm, wherein the alarm is set off when the distance measured by the distance sensor remains below a predetermined reference distance. Further, the alarm may be triggered by distance below a predetermined reference distance over a predetermined duration. In some embodiments, the system may trigger an alarm when light exposure exceeds a predetermined amount. Further, an alarm may further be triggered by exposure exceeding a predetermined amount over a predetermined duration. In yet another embodiment, an alarm may be triggered when outdoor light exposure is below a desired daily amount. It should be noted that a variety of different alarms may be provided when differing event notices are desired, such as in audio tone, visually, haptic pattern, or the like. For example, the alarm for distance warning may differ from the alarm for light exposure. In some embodiments, the microprocessor and/or the digital card data logger are wirelessly connected to the TOF distance sensor and the real time clock.

As a nonlimiting example of the system, a device comprising an infrared time-of-flight (TOF) distance sensor operatively connected to a real time clock controlled by a microprocessor coupled to a digital card data logger may be provided. In one embodiment, the TOF distance sensor has nanosecond technology. In one embodiment, the microprocessor is an Arduino microprocessor. In one embodiment, the digital card data logger is a micro secure digital card data logger. In one embodiment, the device further comprises a lithium polymer battery.

In one embodiment, provided herein is a method of reducing the risk of, preventing or treating a disease in a subject. In one embodiment, the disease is an eye disease. In one embodiment, the disease is myopia. In some embodiments, the method comprises mounting or positioning a monitoring device near the eyes of a wearer, and monitoring parameters of interest. For example, the monitoring device, such as the aforementioned system or select components of the system (e.g. distance and/or light exposure sensor), may be mounted to spectacle frames or the like. Further, the device may monitor parameter(s), such as viewing distances, light exposure, and/or the like. As parameter(s) are monitored, time data is collected and associated with the data collected so that duration can be easily be determined. If desired, the monitored parameter data and/or time data may be stored.

As a nonlimiting example, time data associated with viewing distance, time data associated with light exposure, or the like may be gathered and/or stored. In some embodiments, the method may also include the step of monitoring the parameters for certain events, such as viewing distances below a predetermined amount, light exposure exceeding a predetermined level, and/or the like. These events may be utilized to trigger alarm(s) in some embodiments. Additionally, some embodiments may also monitor duration of the instances of interest. As a nonlimiting example, the method may further comprise alarm(s) that are triggered by distances below a predetermined amount, light exposure exceeding a predetermined level or the like. Further, the alarm(s) may also require distance or exposure to be sustained for a set duration before the alarm is triggered. The alarm(s) may be auditory, visual, or both. In some embodiments, different alarms may be provided depending on the event detected. For example, a first alarm may be provided to indicate viewing distances should be increased to reduce vision impairment risk and/or a second alarm may be provided to indicate light exposure should be reduced or break from screen/monitor/television viewing should be taken. Nonlimiting examples of events of interest may comprise viewing materials too closely (e.g. ≤30 cm), near to near intermediate viewing (e.g. ≤70 cm) exceeding a predetermined time (e.g. ≥20 min.) without a break, and/or not getting enough outdoor light exposure (e.g. at least 75 minutes of exposure at >1000 lux) for the day. As a nonlimiting example, the exemplary system discussed above comprising an infrared time-of-flight (TOF) distance sensor and a real time clock controlled by a microprocessor coupled to a digital card data logger may be utilized in the method discussed.

In some embodiments, a diagnostic method for determining risk factor of a disease in a subject may be provided. A combination of one or more of the steps from the aforementioned method may be utilized in the diagnostic method(s). The steps of the diagnostic method may be performed with the system discussed previously above. Further, the risk of disease may be diagnosed by characterizing near work behavior of the subject, light exposure, or a combination thereof. In one embodiment, the systems and methods may allow risk assessment of refractive error development based on viewing behavior. In one embodiment, the sensor may wirelessly communicate with the processor, storage, clock and/or other components of the system. In one embodiment, the disease is an eye disease. In one embodiment, the disease is myopia. Nonlimiting examples of events of interest may comprise viewing materials too closely (e.g. ≤30 cm), near to near intermediate viewing (e.g. ≤70 cm) exceeding a predetermined time (e.g. ≥20 min.) without a break, and/or not getting enough outdoor light exposure (e.g. at least 75 minutes of exposure at >1000 lux) for the day.

As discussed previously regarding the system, the methods also involve alerts to the wearer. In some embodiments, the wearer may be alerted when one or more of the major behavior(s) believed to be risk factors for myopia is detected: 1) reading material too close (for example 30 cm or closer), 2) near to near intermediate work duration too long (for example viewing ≤70 cm for ≥20 minutes without a distance viewing break), and/or 3) time spent outdoors below a predetermined amount for the day (for example, ≥75 minutes exposed to >1000 lux at 4:00 pm).

The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

EXAMPLES

Example 1

Generally

Refractive development is regulated by a complex interaction between genetic, environmental, and behavioral factors. Potential influences include time outdoors, near work, physical activity, nutrition and urbanization. An association has been found between myopia and increased time studying and reading. The highest odds for myopia have been shown in subjects that spend low time outdoors and a high time spent performing near work. However, results regarding the influence of near work have been conflicting, with some studies reporting no significant increased risk of myopia onset with increased near work. Inconsistent results concerning the role of near work and myopia onset and progression are likely due to the variable and subjective nature by which near work has traditionally been assessed.

Previous studies evaluating near work in children have been performed with parent questionnaires, which are subject to poor recall and parent biases. In addition, the nature in which survey items are worded has led to inconclusive results. For example, some studies have used education, intelligence, and occupations requiring near work as a surrogate for near work. Other studies have relied on diaries to quantify near work, which was limited by subject compliance.

Another technique previously utilized to assess working distance is the experience sampling method. With the experience sampling method, a pager is dispensed to subjects was used to send alerts throughout the day. Following each page, subjects were asked to complete a self-report about activities at the moment of the page. While this technique provides "real-time" sampling of activities and was shown to be capable of detecting the proportion of time spent doing near work, only discreet time points are sampled, typically 5-6 times throughout each day, and results depend on the response rate of the subject, averaging approximately 87%.

These subjective methods of near work quantification provide only a crude assessment of viewing behavior. A commonly used metric calculated from questionnaires is "diopter hours," which allows various near activities and viewing distances to be weighted. However, this metric does not describe complex details of viewing behavior that may influence eye growth, such as the temporal patterns of near viewing. Relevant viewing behaviors that might affect eye growth include factors such as the duration of each near viewing session, intermittent breaks during near viewing, and absolute viewing distance. Studies in animals have shown that experimental myopia is dependent on the temporal pattern of defocus or form deprivation, rather than the total duration of the myopia-genic stimulus. For example, studies have shown that brief interruptions of form deprivation with normal vision significantly decrease the magnitude of myopia in chicks. Continuous, objective assessment provided by the systems and methods discussed will provide the opportunity to assess such behaviors to understand influence in myopia onset and progression in humans.

The use of wearable electronic monitoring devices, now available for quantifying light exposure, time spent outdoors and activity, and/or the like provides the opportunity to objectively and precisely quantify environmental and behavior factors. Recent studies have provided objective evidence that light exposure is related to time of year, and that myopic children tend to spend less time outdoors than emmetropic children. Importantly, these studies revealed discrepancies between traditional subjective reports and objective data for both adults and children for time spent outdoors. The development and implementation of the systems and methods discussed for continuous, objective measurement will provide an opportunity to measure various aspects of viewing behavior, and can be used with previously validated light exposure and activity monitors, to provide a complete description of visual activity relevant to behaviors associated with eye growth and myopia development.

One such continuously measuring device has been previously developed and tested in adult high and low/non myopes to assess reading distance. The device used ultrasonic technology mounted on a headband to continuously measure and log viewing distance while subjects read a newspaper for 10 minutes. The results showed that the device was repeatable with high sensitivity, and that high myopes had a shorter habitual working distance than low/non myopes. Additionally, the authors found that the subject's self-reported reading distances varied greatly from objective measures, thereby demonstrating the inaccuracies of survey techniques. The improved systems and methods discussed allow for continuous measurements of working distance or the like, which may be utilized to compare objective measures to traditional subjective visual activity questionnaires and logs, and to compare near viewing behaviors between myopic and non-myopic young adults.

Example 2

Instrumentation and Calibration

Figures 2A, 2B, 2C:
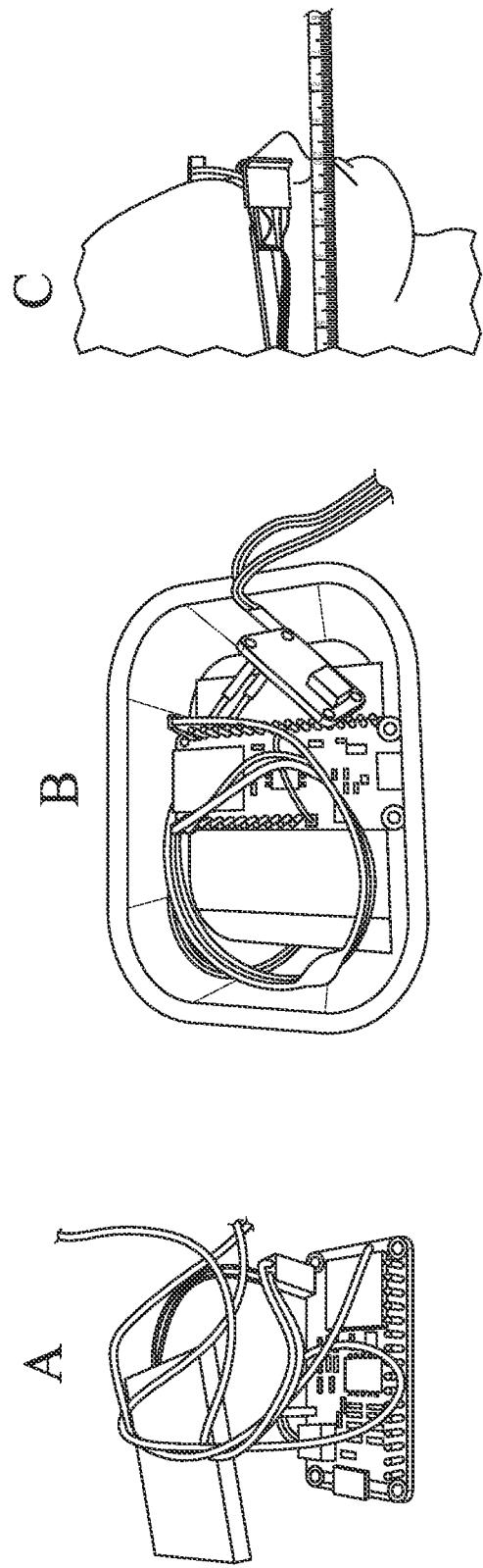
FIGS. 2A-2C depict, in accordance with embodiments herein, 2A) components of the device; 2B) Enclosure with belt clip; 2C) device mounted on spectacle frames for calibration.

As illustrated in FIGS. 2A-2C, a nonlimiting experimental example of the system comprised an infrared time-of-flight (TOF) distance sensor with nanosecond technology and a real-time clock (RTC) controlled by an Arduino microprocessor coupled to a micro secure digital card data logger (all components from Adafruit, USA). FIG. 2A shows the system separated from a housing and frame; FIG. 2B shows the housing and belt clip of the system; and FIG. 2C shows the sensor mounted to frames for calibration. Open-source programming libraries for the TOF, RTC, and data logger components were used to write running code for the device. Power was supplied by a rechargeable 2500 mAh lithium polymer battery to provide greater than 16 hours of continuous distance measurements. The sensor was 1×1×0.2 cm, with a 1 m wire leading to the microprocessor. The device was programmed to collect data continuously at 1 Hz. Four devices were constructed, and each was tested for known distances from 0.05 to 2 m in 0.05 m intervals to generate a unique calibration. The calibration for each device was highly repeatable and the data were free from spurious measurements. The beam diameter was determined for distances from 0.1 to 0.6 m in 0.1 m intervals using an infrared viewer.

Example 3

Implementation

The sensor was mounted on the right temple of a spectacle frame and directed approximately 4° nasally, so that the beam is aligned at the midpoint at 0.40 m. The midline beam orientation at 0.40 m matches the alignment of the eyes at typical near viewing distances. Devices will be mounted to subjects' habitual spectacle frame, or on a provided frame with plano lenses if the subject wears contact lenses or does not need spectacles. The wire runs along the right temple, behind the ear, and to a separate enclosure, 9×6×4 cm, with belt clip that holds remaining components of the system.

Following each full day of wear, data collected by the system may be downloaded and binned into 0.10 m intervals to calculate the number of minutes per day spent viewing distances from 0.10 to 1.0 m. Various categories may be classified, ranging from from "extremely near" viewing (10-20 cm) to "distance" viewing (>100 cm, Table 1).

TABLE 1

Viewing distance classifications from 10 to >100 cm with example activities for each category.

| Viewing Distance | Classification | Example activities |
| --- | --- | --- |
| ≥10 and <20 cm | Extremely near | Hand held devices |
| ≥20 and <30 cm | Very near | Hand held devices, printed material |
| ≥30 and <40 cm | Fairly near | Printed material |
| ≥40 and <50 cm | Near | Printed material, computer monitor |
| ≥50 and <60 cm | Moderately near | Computer monitor |
| ≥60 and <70 cm | Near intermediate | Computer monitor |
| ≥70 and <80 cm | Intermediate | Conversing with others |
| ≥80 and <90 cm | Moderately intermediate | Conversing with others |
| ≥90 and <100 cm | Far intermediate | Conversing with others, cooking |
| ≥100 cm | Distance | Television viewing, driving, outdoor activity |

Objective diopter hours will be calculated from the system data using equation 1.

$$\text{Diopter Hours} = [(3 \times \text{hours of 10 cm-50 cm}) + (2 \times \text{hours of 51 cm-80 cm}) + (1 \times 81 \text{ cm-100 cm})]$$

Example 4

Results

Figures 3A, 3B:
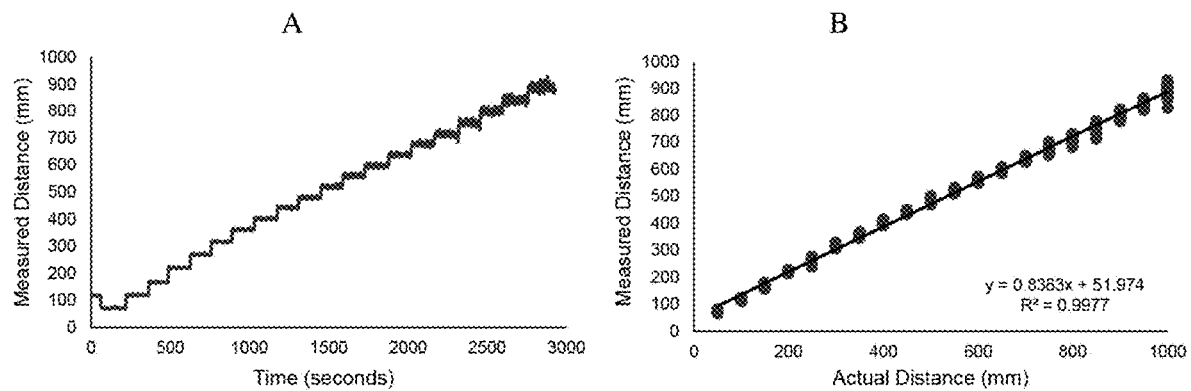
FIGS. 3A-3B depict, in accordance with embodiments herein, 3A) for calibration, the device was positioned 50 mm from a wall and moved outward an additional 50 mm every 2 minutes; 3B) linear calibration for actual versus recorded distances from the device.
Figures 4A, 4B:
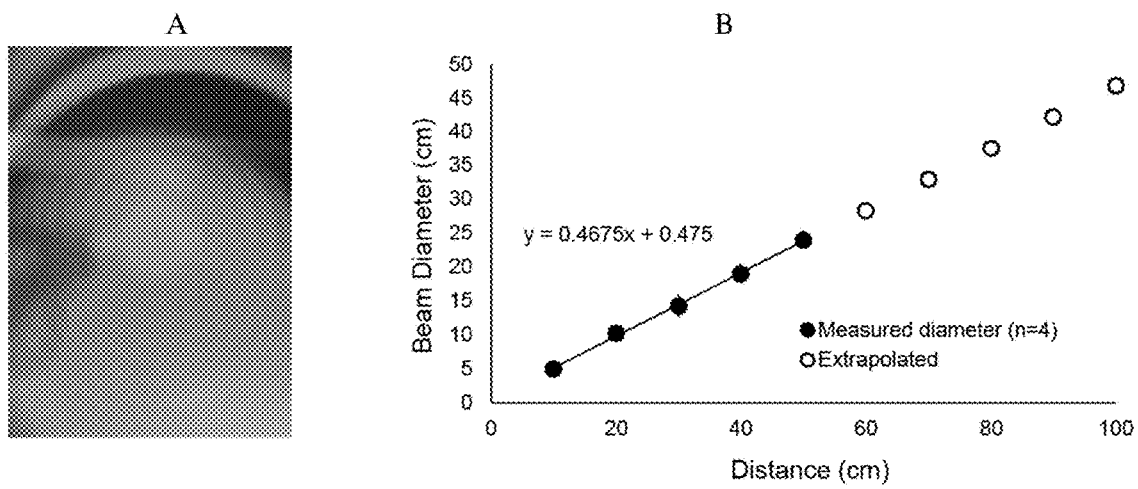
FIGS. 4A-4B depict, in accordance with embodiments herein, 4A) infrared beam as seen through an infrared viewer projected against a concentric cm scale; 4B) beam diameter with distance for 4 devices.

The devices demonstrate a linear correlation with measured distances, 0.05 to 1.2 m (y=0.9446x+0.422, FIG. 3A showing measured distance over time and 3B showing measured distance vs actual distance). Beyond 1.2 m, distances were out of range. The standard deviation of the measurement at 0.05 m was ±0.002 m, at 0.40 m was ±0.003 m, and at 1.0 m was ±0.012 m. Beam diameter for near distances ranged from 5 to 20 cm and increased linearly with distance (FIG. 4A showing an image of the beam and 4B showing beam diameter vs distance).

Figure 5:
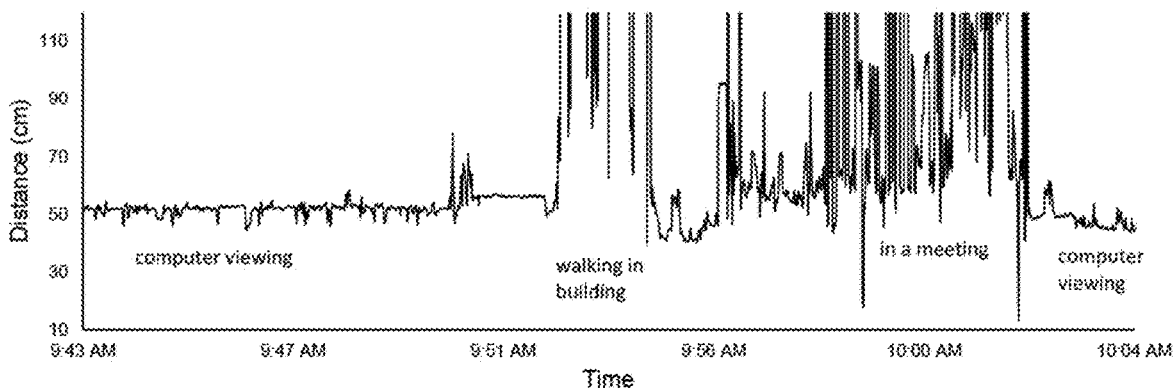
FIG. 5 depicts, in accordance with embodiments herein, continuous monitoring for 20 minutes as the subject was at a desk and walking in building (Vertical spikes represent near to distance viewing)
Figures 6A, 6B, 6C, 6D:
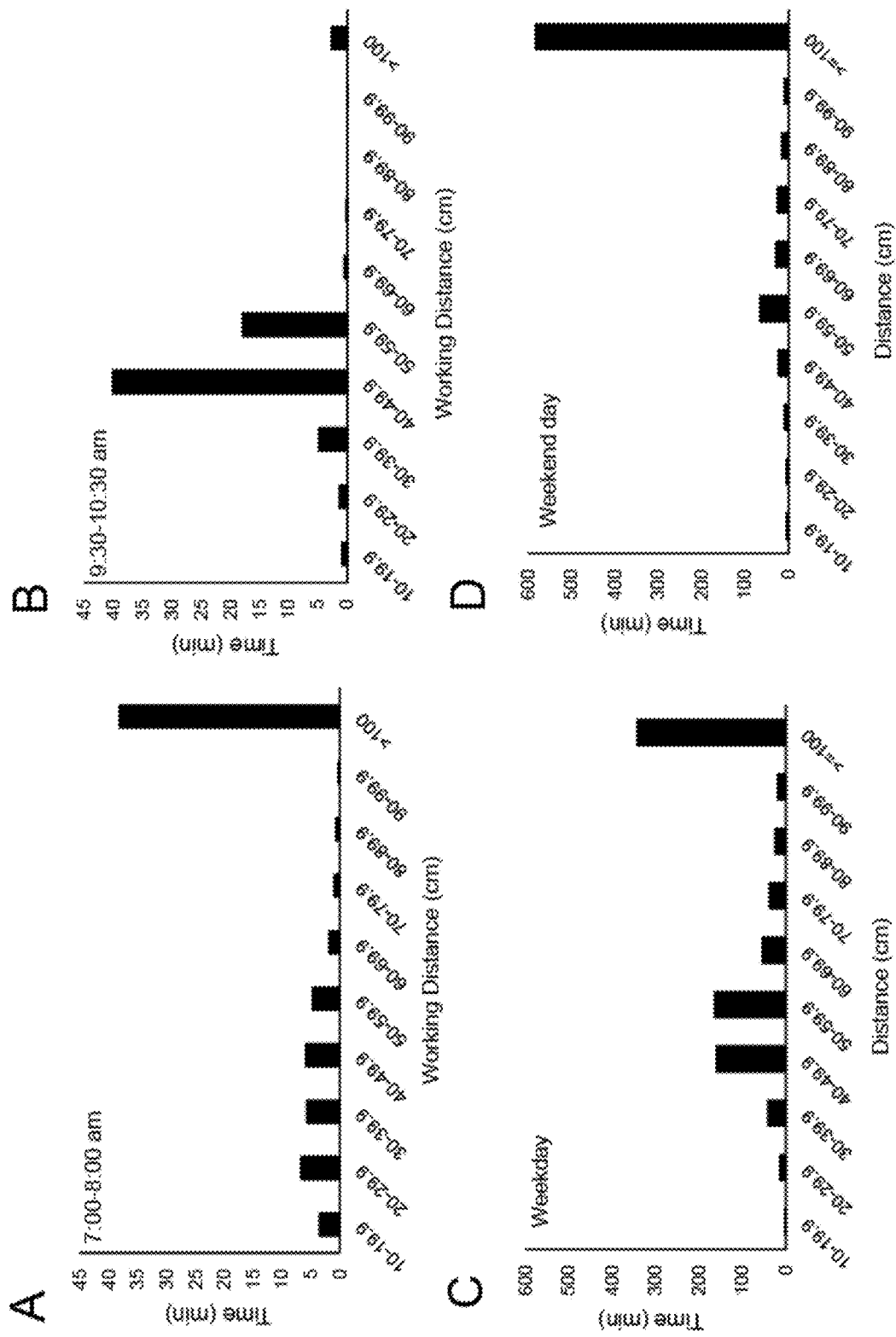
FIGS. 6A-6D depict, in accordance with embodiments herein, one hour recording showing viewing distances while 6A) driving, 6B) working at computer, and full day recording showing viewing distances for 6C) a weekday and 6D) a weekend day.

Pilot studies have shown that measured distances with the system are well correlated with subject's diary entries. A raw trace from a 20 minute period of subject wear is shown in FIG. 5. Data for an adult subject who wore the system for 12-16 hours per day for 7 days are shown in FIGS. 6A-6D. For a one hour time period at home and driving, the majority of time was spent viewing in the distance (≥100 cm) range (FIG. 6A). For one hour during work, most time was spent viewing near to moderately near (~40-60 cm) distances, and less than 5 minutes was spent on distance (≥100 cm) viewing (FIG. 6B). For an entire 14 hour work day, over 8 hours was spent viewing fairly near to intermediate (~30-80 cm) distances (FIG. 6C). For a 14 hour weekend day, less than 3 hours was spent viewing fairly near to intermediate (~30-80 cm) distances (FIG. 6D).

Example 5

Prototypes

Prototype devices and pilot data collected in human subjects demonstrate the validity and feasibility of continuous, objective assessment of near and intermediate viewing distances using the systems and method. The first objective quantification of daily viewing distances for young adults is presented. These results support further use of the device to assess differences between groups of subjects who are emmetropic and myopic to begin to understand the influence of near work and viewing behavior in myopia.

In one embodiment, data from the system is stored locally and accessible to the user. In some embodiments, new data collected by the system may be periodically transmitted or sent, such as nighttime when the system is not worn, to remote storage, such as a computer, laptop, cloud storage, or the like. In one embodiment, the system uses an infrared, time-of-flight sensor and a narrow beam laser with nanosecond technology to detect a range from 5 cm to 120 cm.

The reliable measurable range of the experimental system was limited to 5-120 cm, and therefore, distances greater than 100 cm could not be quantified and were classified as "distance" for the purpose of this study. However, other embodiments may utilize sensors with a greater range. Another limitation was that the device was mounted to the frame of the glasses and did not follow eye rotation. This may have resulted in an underestimation of near viewing distances if subjects rotated their eyes downwards to read. The inventors minimized this confounding factor by encouraging subjects to turn their head towards their viewing targets. Lastly, the device transmits data via a cord leading to an enclosure with a belt clip. The cord would likely present some difficulty with subjects who are involved in sports or other vigorous physical activity. The adult subjects did not note problems in the current study, even during exercise. In one embodiment, the instrument is optimized by designing the components such that data can be stored within the sensor and eliminating the need for a wired enclosure.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps, some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A system for objective assessment, the system comprising:
   a power source;
   a processor;
   a distance sensor coupled to the processor, wherein the distance sensor is positioned to continuously measure viewing distances;
   a clock providing time data that is associated with the viewing distances measured; and
   data storage recording the time data associated with the viewing distances measured and the viewing distances measured, wherein the processor utilizes the time data and the viewing distances measured to calculate diopter hours to diagnose vision impairment risk,
   wherein the diopter hours is calculated as [(3×hours of the time data associated with the viewing distances measured between 10 cm≤50 cm)+(2×hours of the time data associated with the viewing distances measured between 50 cm≤80 cm)+(1×hours of the time data associated with the viewing distances measured between 80 cm≤100 cm)].

2. The system of claim 1, wherein the distance sensor is removably mounted on a spectacle frame.

3. The system of claim 2, wherein the distance sensor is positioned near a temple of the spectacle frame.

4. The system of claim 1 further comprising an alert mechanism, wherein the alert mechanism is triggered when the measured distance is less than a predetermined reference distance.

5. The system of claim 4, wherein the predetermined reference distance is ≤30 cm.

6. The system of claim 4, wherein the alert mechanism comprises an alarm, wherein the alarm is triggered when the measured distance is less than a predetermined reference distance for greater than a predetermined duration.

7. The system of claim 1 further comprising a light sensor coupled to the processor for detecting illuminance of light.

8. The system of claim 1 further comprising an alert mechanism, wherein the alert mechanism is triggered when outdoor light exposure is below a predetermined exposure amount for less than a predetermined amount of time in a day.

9. The system of claim 1, wherein the viewing distances measured are classified as follows to assess myopia risk:
10 cm≥extremely near>20 cm,
20 cm≥very near>30 cm,
30 cm≥fairly near>40 cm,
40 cm≥near>50 cm,
50 cm≥moderately near>60 cm,
60 cm≥near intermediate>70 cm,
70 cm≥intermediate>80 cm,
80 cm≥moderately intermediate>90 cm,
90 cm≥far intermediate>100 cm, and
≥100 cm as distance.

10. A method for objective assessment, the method comprising:
positioning a distance sensor to continuously measure viewing distances;
capturing time data associated with the viewing distances measured;
storing the time data and the viewing distances measured; and
analyzing the viewing distance measurements and the time data associated with the viewing distances measured to calculate diopter hours to diagnose vision impairment risk,
wherein diopter hours is calculated as [(3×hours of the time data associated with the viewing distances measured between 10 cm≤50 cm)+(2×hours of the time data associated with the viewing distances measured between 50 cm≤80 cm)+(1×hours of the time data associated with the viewing distances measured between 80 cm≤100 cm)].

11. The method of claim 10 further comprising the step of triggering an alert mechanism when the viewing distance measured is less than a predetermined reference distance.

12. The method of claim 11, wherein the alert mechanism comprises an alarm.

13. The method of claim 10 further comprising positioning a light sensor to detect illuminance of light.

14. The method of claim 13 further comprising triggering an alert mechanism when outdoor light exposure is below a predetermined exposure amount for less than a predetermined amount of time in a day.

15. The method of claim 10, wherein the distance sensor is removably mounted on a spectacle frame.

16. The method of claim 10, wherein the distance sensor is positioned near a temple of the spectacle frame.

17. The method of claim 10, wherein the viewing distances measured are classified as follows to assess vision impairment risk:
10 cm≥extremely near>20 cm,
20 cm≥very near>30 cm,
30 cm≥fairly near>40 cm,
40 cm≥near>50 cm,
50 cm≥moderately near>60 cm,
60 cm≥near intermediate>70 cm,
70 cm≥intermediate>80 cm,
80 cm≥moderately intermediate>90 cm,
90 cm≥far intermediate>100 cm, and
≥100 cm as distance.

18. The method of claim 17, wherein the vision impairment risk is an eye disease selected from myopia.

* * * * *